US012611524B2

(12) United States Patent
Cole et al.

(10) Patent No.: US 12,611,524 B2
(45) Date of Patent: Apr. 28, 2026

(54) SYSTEMS AND METHODS FOR A CATHETER STABILIZATION AND OCCLUDER APPARATUS

(71) Applicant: Dignity Health, San Francisco, CA (US)

(72) Inventors: Tyler Cole, San Francisco, CA (US); Dakota Graham, San Francisco, CA (US); Michael Bohl, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 869 days.

(21) Appl. No.: 17/759,434

(22) PCT Filed: Dec. 10, 2020

(86) PCT No.: PCT/US2020/064305
§ 371 (c)(1),
(2) Date: Jul. 25, 2022

(87) PCT Pub. No.: WO2021/158284
PCT Pub. Date: Aug. 12, 2021

(65) Prior Publication Data
US 2023/0095825 A1      Mar. 30, 2023

Related U.S. Application Data

(60) Provisional application No. 62/978,492, filed on Feb. 19, 2020, provisional application No. 62/969,711, filed on Feb. 4, 2020.

(51) Int. Cl.
*A61M 25/04*      (2006.01)
*A61M 25/02*      (2006.01)

(52) U.S. Cl.
CPC ..... *A61M 25/04* (2013.01); *A61M 2025/0213* (2013.01); *A61M 2025/024* (2013.01);
(Continued)

(58) Field of Classification Search
CPC .......... A61M 25/02; A61M 2025/0213; A61M 2025/024; A61M 2025/028; A61M 25/04; A61M 2210/0687; A61N 1/0539
See application file for complete search history.

(56) References Cited

U.S. PATENT DOCUMENTS 6,482,183 B1 *   11/2002   Pausch ................ A61J 15/0015
                                                          604/174
2006/0058738 A1      3/2006   Ponzi et al.
(Continued)

FOREIGN PATENT DOCUMENTS

| CN | 110404149 A | 11/2019 |
|----|-------------|---------|
| DE | 19749741 C1 | 11/1998 |
| EP | 1048320 A2  | 11/2000 |

OTHER PUBLICATIONS

Patent Cooperation Treaty, International Search Report and Written Opinion, International Application No. PCT/US2020/064305, dated Apr. 9, 2021, 5 pages.
(Continued)

*Primary Examiner* — Nilay J Shah
(74) *Attorney, Agent, or Firm* — Polsinelli PC

(57)      ABSTRACT

Various embodiments of a catheter stabilizer that includes a retention body and an occluder for positioning within a burr hole or other channel in the body for occlusion and stabilization of a catheter during a surgical procedure are described herein. Specifically, the retention body further defines a channel configured to be oriented above the burr hole; in some embodiments the channel can provide reference for drilling a burr hole after placement of the retention body. The catheter stabilizer further includes an occluding arm, (Continued)

which can be positioned across an opening of the burr hole
for receiving and occluding a catheter within the burr hole.

15 Claims, 24 Drawing Sheets

(52) U.S. Cl.
CPC ... *A61M 2025/028* (2013.01); *A61M 2205/04*
*(2013.01); A61M 2210/0687* (2013.01)

(56) References Cited

U.S. PATENT DOCUMENTS

| | | | | |
|---|---|---|---|---|
| 2007/0142784 A1* | 6/2007 | Dikeman | ............. | A61M 25/02 |
| | | | | 604/174 |
| 2007/0249980 A1* | 10/2007 | Carrez | ................. | A61M 25/02 |
| | | | | 602/47 |
| 2014/0155859 A1 | 6/2014 | Bonde | | |
| 2015/0119808 A1 | 4/2015 | Khalaj | | |
| 2018/0311007 A1 | 11/2018 | Tyler, II et al. | | |

OTHER PUBLICATIONS

European Patent Office, Extended European Search Report, Application No. 20917983.7, Feb. 9, 2024, 15 pages.

* cited by examiner

700

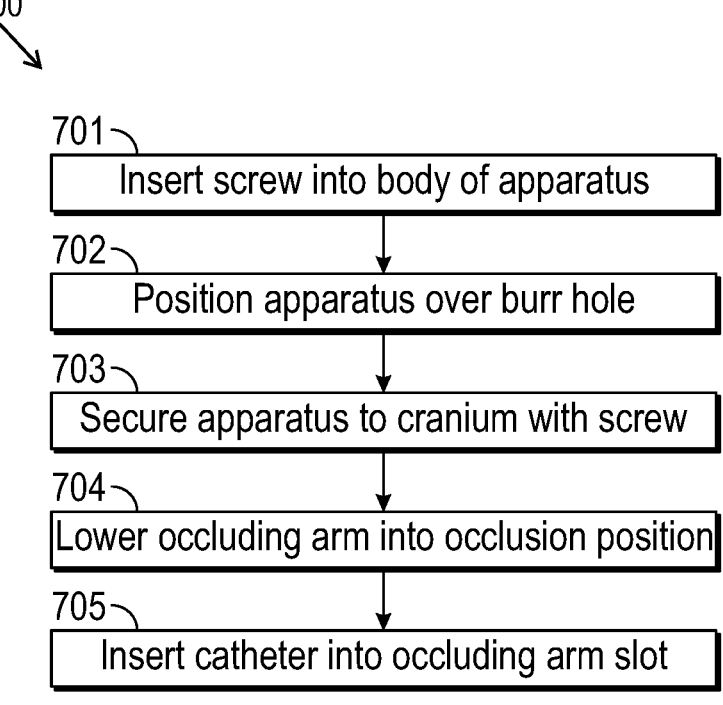

701 ──┐
Insert screw into body of apparatus

702 ──┐
Position apparatus over burr hole

703 ──┐
Secure apparatus to cranium with screw

704 ──┐
Lower occluding arm into occlusion position

705 ──┐
Insert catheter into occluding arm slot

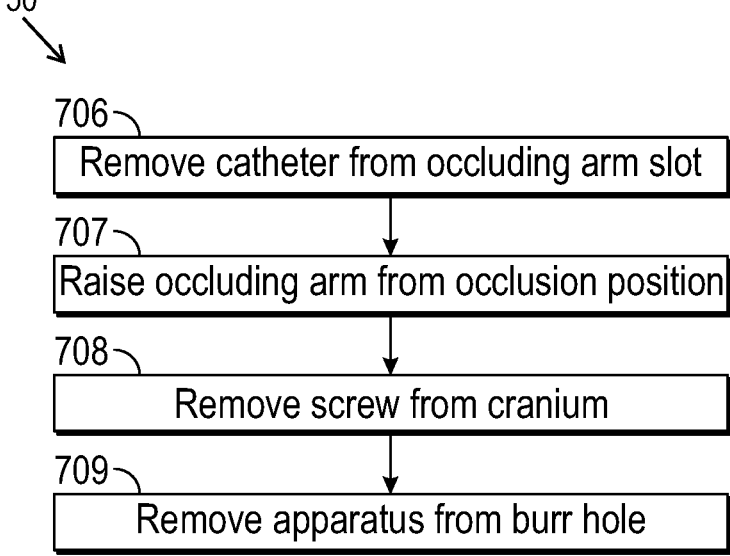

706 ──┐
Remove catheter from occluding arm slot

707 ──┐
Raise occluding arm from occlusion position

708 ──┐
Remove screw from cranium

709 ──┐
Remove apparatus from burr hole

FIG. 19

SYSTEMS AND METHODS FOR A CATHETER STABILIZATION AND OCCLUDER APPARATUS

CROSS-REFERENCE TO RELATION APPLICATIONS

The present application claims priority under 35 U.S.C. § 119 to U.S. Provisional Patent Application No. 62/969,711; filed Feb. 4, 2020 and U.S. Provisional Patent Application No. 62/978,4492; filed Feb. 19, 2020, which are incorporated by reference in its entirety herein.

FIELD

The present disclosure generally relates to medical devices; and in particular, to an apparatus and associated method for stabilizing a catheter during a surgical procedure.

BACKGROUND

During surgical placement of a catheter in the body, it is often necessary to perform other aspects of a surgery, while also ensuring that the catheter remains stabilized or otherwise held in place. In many surgical applications, this may be frequently done using an extra "set of hands" in the operating room. During surgery, it is also sometimes necessary to occlude, or pinch shut, a catheter while the catheter is in position. For example, during placement of a valve, the catheter has to be stabilized and occluded first in order to safely and securely position the valve within the body near the catheter before securing the catheter to the valve. The task of stabilizing and occluding the catheter is often cumbersome and requires at least one extra pair of hands to occlude and stabilize the catheter. Further, current retractor devices such as metal retractors commonly used in surgical applications, are not compatible with electromagnetic (EM) neuronavigation as they are typically comprised of ferromagnetic materials that interfere. During many shunt procedures that use EM neuronavigation, a typical metal retractor would need to be removed during navigation and placed again after navigation.

It is with these observations in mind, among others, that various aspects of the present disclosure were conceived and developed.

BRIEF DESCRIPTION OF THE DRAWINGS

FIG. 18 is a diagram showing a method of insertion of the catheter stabilizer; and FIG. 19 is a diagram showing a method of removal of the catheter stabilizer.

Corresponding reference characters indicate corresponding elements among the view of the drawings. The headings used in the figures do not limit the scope of the claims.

DETAILED DESCRIPTION

Figure 1:
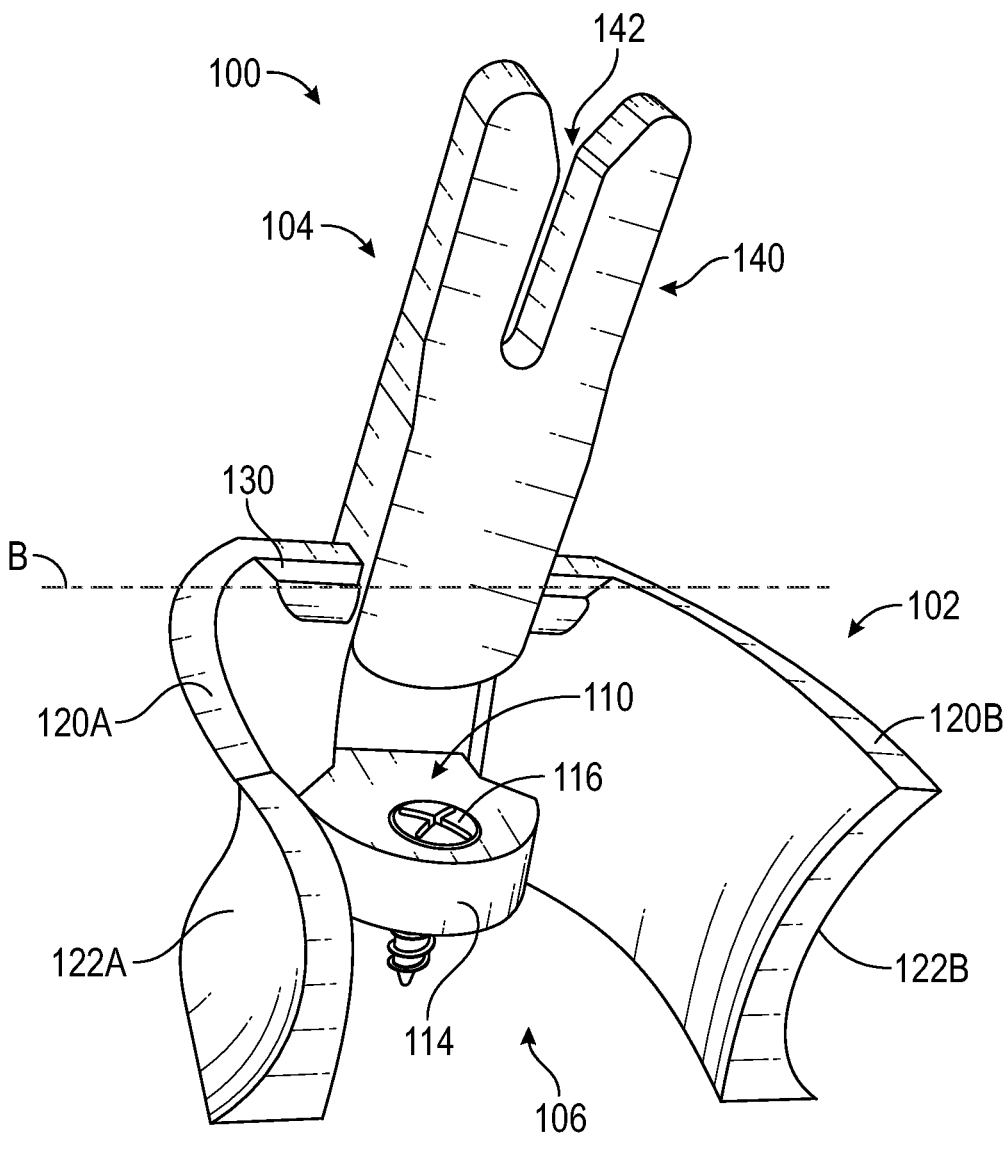
FIG. 1 is a perspective view showing a first embodiment of a catheter stabilizer defining a retention body and an occluding arm.

Various embodiments of a catheter stabilizer apparatus and associated method for stabilizing a catheter within a cranial burr hole are disclosed herein. In a primary embodiment, the catheter stabilizer is configured to be positioned and secured over a burr hole bored in a cranium of a patient during surgery. In some embodiments, the catheter stabilizer includes a retention body including one or more retention members for exposing the burr hole and retracting back cranial tissue of an incision to allow a clear workspace. The retention body further defines a channel configured to be oriented above the burr hole; in some embodiments the channel can provide reference for drilling a burr hole after placement of the retention body. The catheter stabilizer further includes an occluding arm, which can be positioned across an opening of the burr hole for receiving and occluding a catheter within the burr hole. Alternatively, the occluding arm may be positioned away from the burr hole to expose the channel and allow the surgeon to work within the burr hole. In some embodiments, the retention body is configured to be secured to the cranium of the patient. In one method of installation, the catheter stabilizer is inserted into an incision positioned over the burr hole and secured to the cranium. The occluding arm is then lowered into an "occlusion" position and the catheter inserted into a slot of the occluding arm. In some embodiments, the catheter stabilizer apparatus can be used for retracting cranial tissue and stabilizing/occluding catheters during new shunt placement and shunt revision procedures. Referring to the drawings, embodiments of a catheter stabilizer are illustrated and generally indicated as 100 in FIGS. 1-19.

Figure 2:
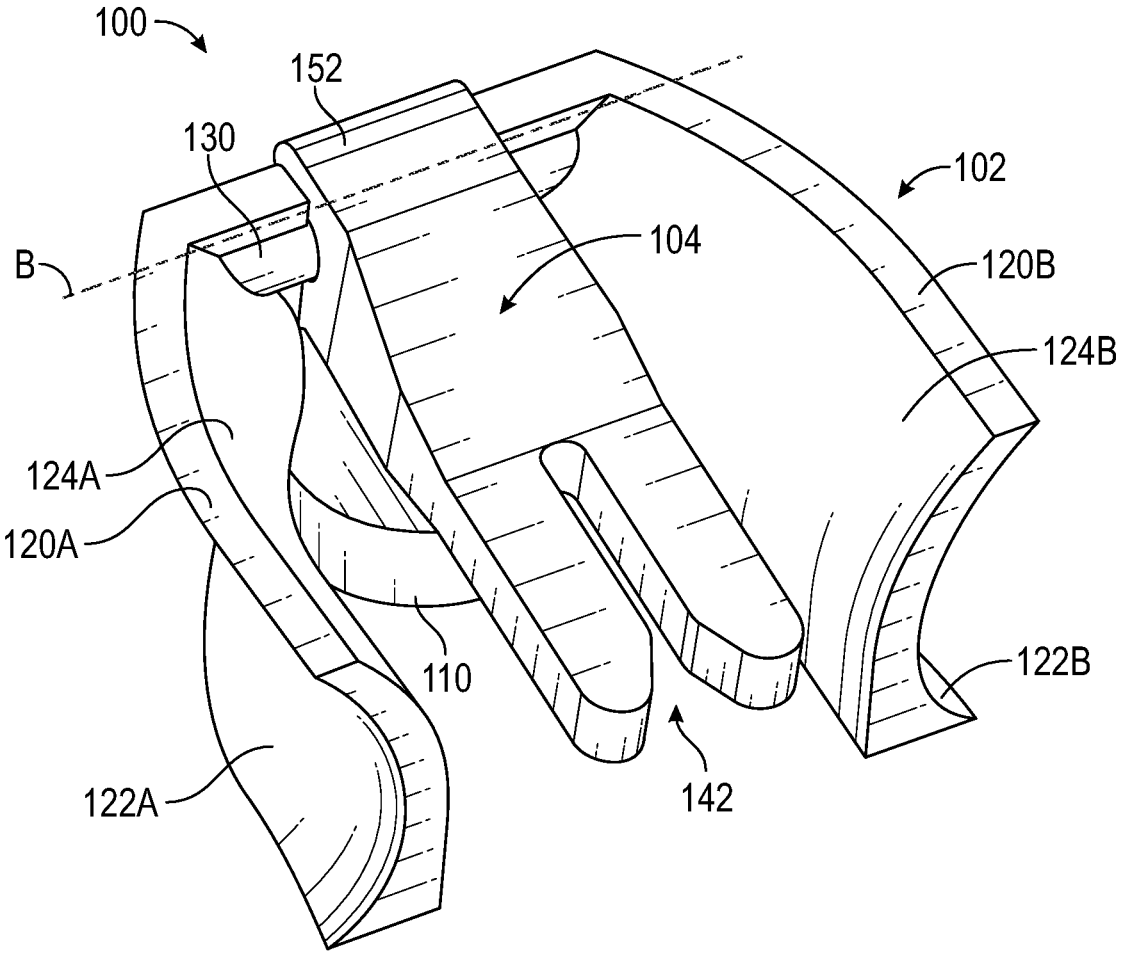
FIG. 2 is a perspective view showing the catheter stabilizer of FIG. 1 showing the occluding arm in an "occluding" position.
Figure 17A:
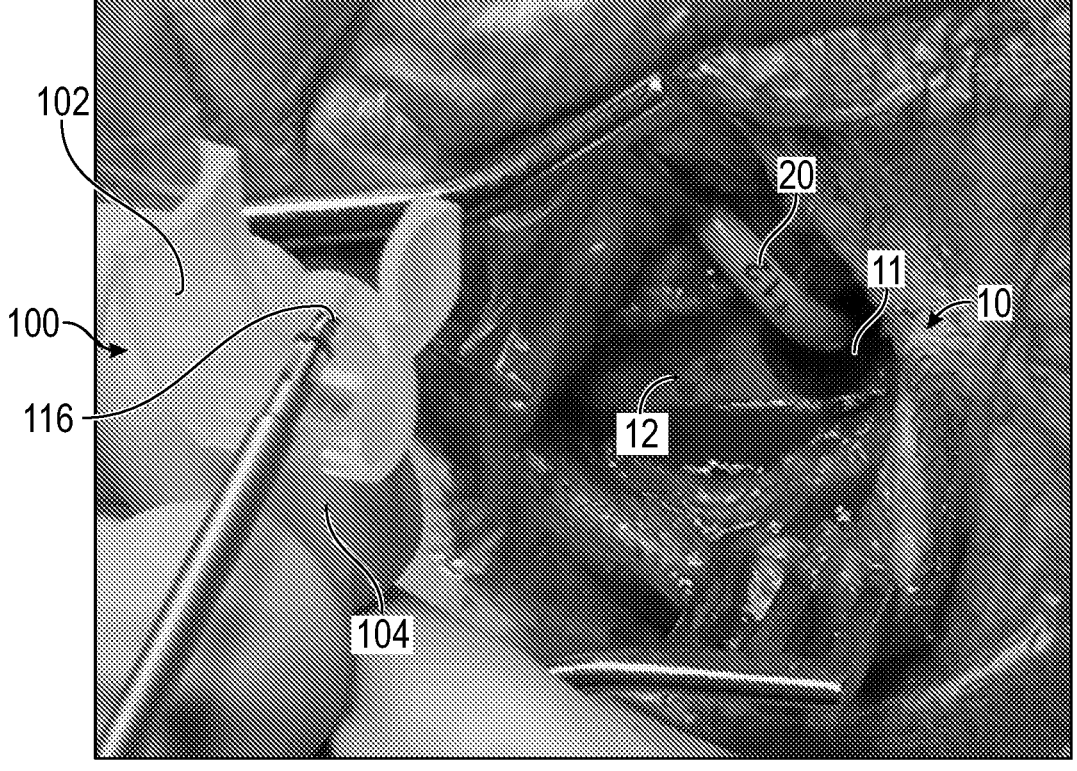
FIG. 17A is a first sequential view showing a screw being engaged with the retention body of the catheter stabilizer of FIG. 1 prior to insertion within an incision.
Figure 17B:
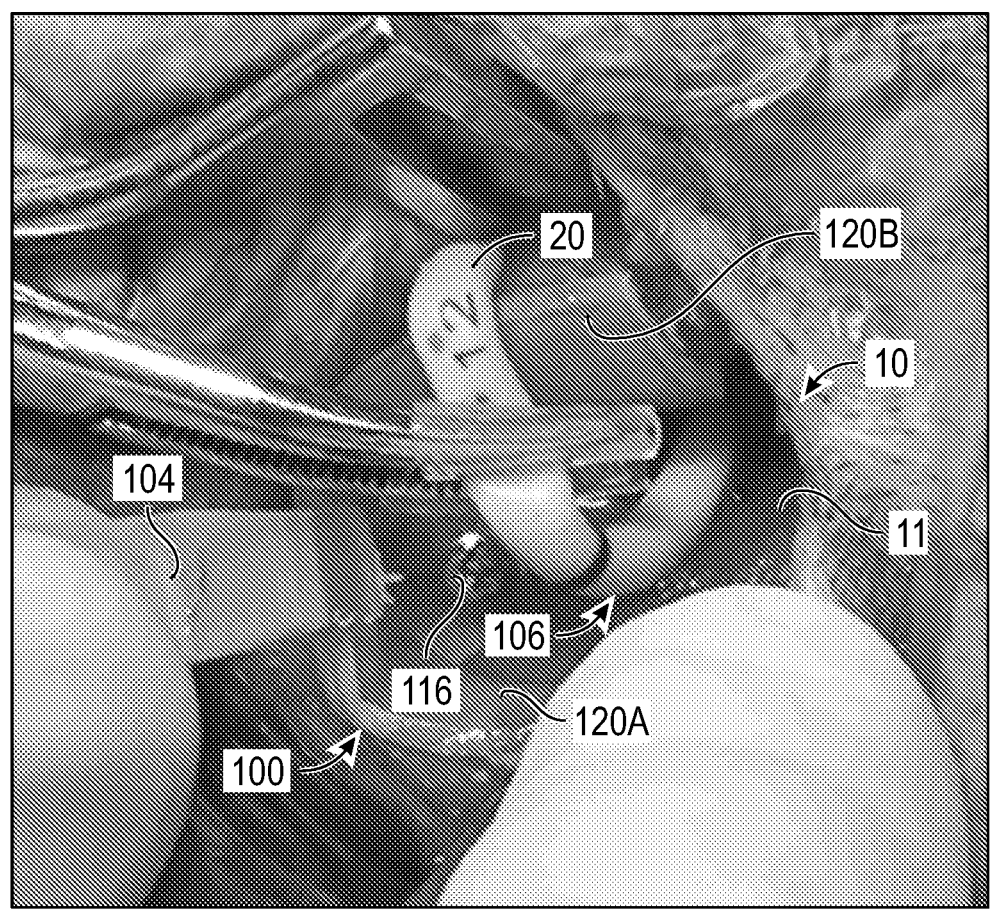
FIG. 17B is a second sequential view showing the catheter stabilizer of FIG. 1 being positioned over a burr hole in a cranium of a patient.
Figure 17C:
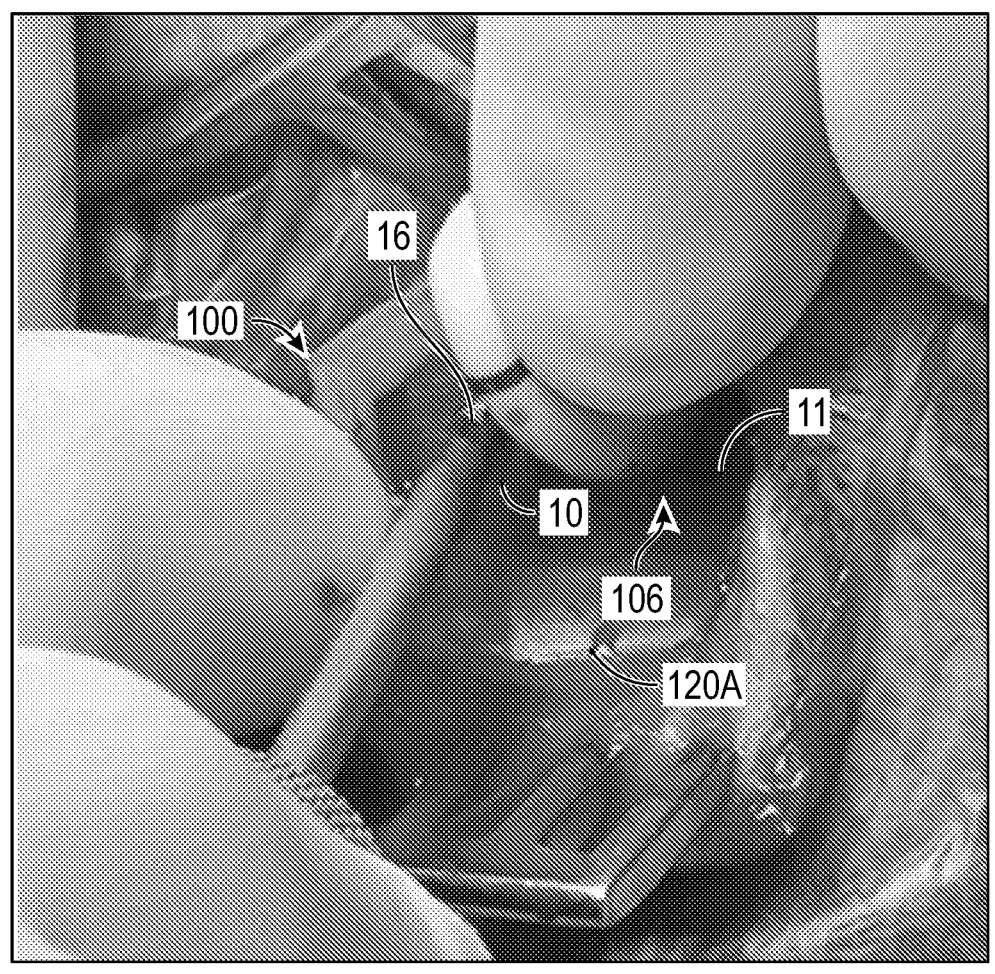
FIG. 17C is a third sequential view showing the catheter stabilizer of FIG. 1 being secured onto a cranium of a patient.

Referring to FIGS. 1-4 and 17A-K, the catheter stabilizer 100 includes a retention body 102 for insertion within an incision 10 (FIG. 17A), the retention body 102 defining a channel 106 defining an axis A (FIG. 3) for alignment with a burr hole 11. The retention body 102 is configured to retract cranial tissue of the incision 10 to expose the burr hole 11. In some embodiments, the retention body 102 is in operative association with an occluder arm 104, the occluder arm 104 configured to be positioned across the channel 106 to receive and occlude a catheter 20. As shown in FIG. 1, the retention body 102 further includes an engagement point 110 defining a perforation 113 (FIG. 3) through a surface 112 configured to contact the cranium for insertion of a securing member 116 into the cranium. FIG. 1 shows occluder arm 104 of the catheter stabilizer 100 in an "open" configuration with the occluder arm 104 rotated about an axis B away from the channel 106. In the "open" configuration of FIG. 1, the channel 106 and engagement point 110 are exposed. In FIG. 2, the occluding configuration is shown in an "occlusion" position with the occluder arm 104 rotated about the axis B such that the occluder arm 104 is positioned across the channel 106. In operation, as shown in FIG. 17B, the catheter 20 is passed through the channel 106 of the catheter stabilizer 100. As further shown, the occluder arm 104 defines a receptacle 142 associated with a free end 140 of the occluder arm 104 for insertion and occlusion of a catheter 20 (FIG. 17E).

Figure 3:
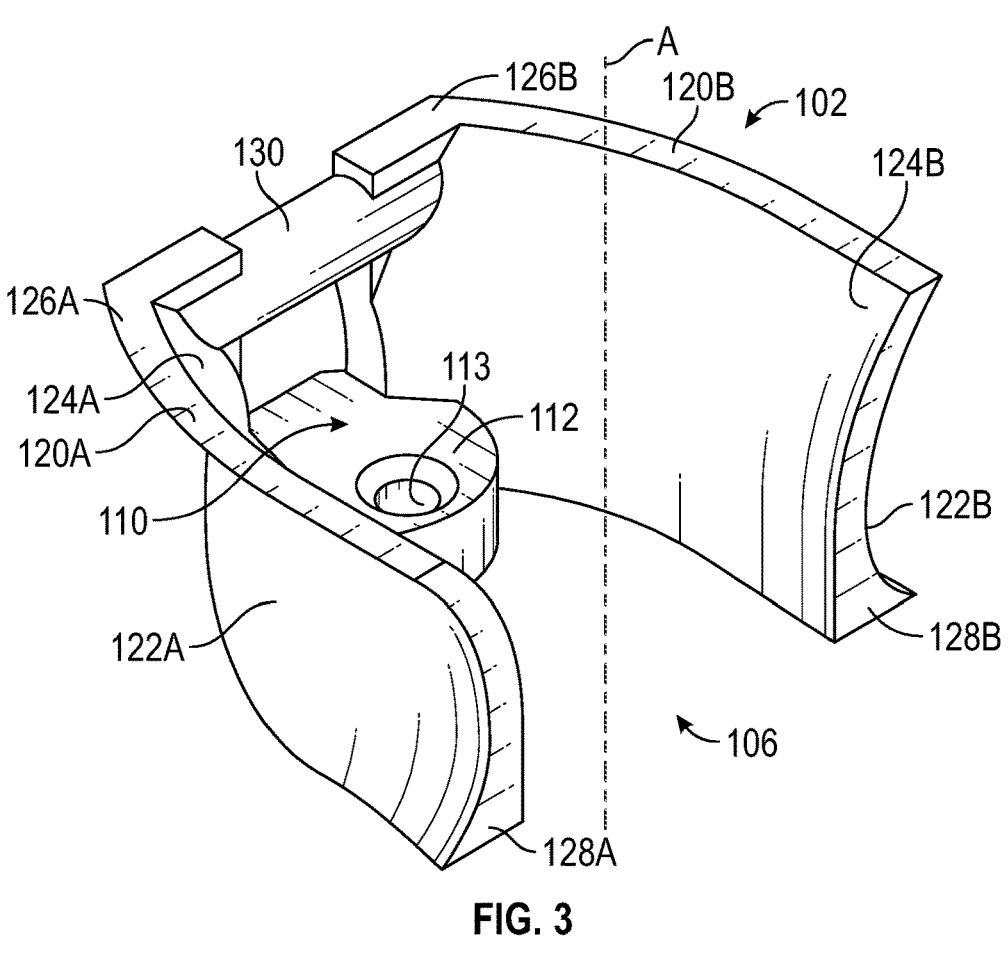
FIG. 3 is a perspective view showing the catheter stabilizer of FIG. 1 with the occluding arm removed.

As discussed above, the retention body 102 includes one or more retention members 120; in the embodiment shown in FIGS. 1-4 and 17A-K, the retention body 102 defines a first retention member 120A and an opposite second retention member 120B that collectively form the channel 106, as shown specifically in FIG. 3. In some embodiments, the retention members 120 are integral with the retention body 102, as shown in the embodiment of FIGS. 1-4, and in other embodiments coupled to one another by a joint 260, such as in the embodiment of FIGS. 5-8. As shown, the retention members 120A and 120B each define a proximal portion 126A and 126B and a distal portion 128A and 128B, respectively. In some embodiments, the retention members 120 each define a concave outer surface 122 for engagement with cranial tissue and an inner surface 124 that at least partially forms the channel 106. In some embodiments, an underside (not shown) of the retention body 102 (and retention body 202 of embodiment 200 illustrated in FIG. 5) also defines a generally concave surface to aid in conformity to the cranium. The retention body 102 further includes an engagement rod 130 defined between each proximal portion 126A and 126B of the first and second retention members 120A and 120B and configured to receive a hand 152 of the occluder arm 104. The engagement rod 130 is located at a junction defined between the first and second retention members 120A and 120B and defines the axis B (FIG. 1) that the occluding arm 104 is rotated around. In some embodiments, the catheter stabilizer 100 including the retention body 102 and the occluder 104, as well as in other embodiments 200, 300, 400 and 500 described herein, are manufactured from a non-ferrous or non-ferromagnetic material such as medical-grade vinyl, plastic or another suitable material.

Figure 4:
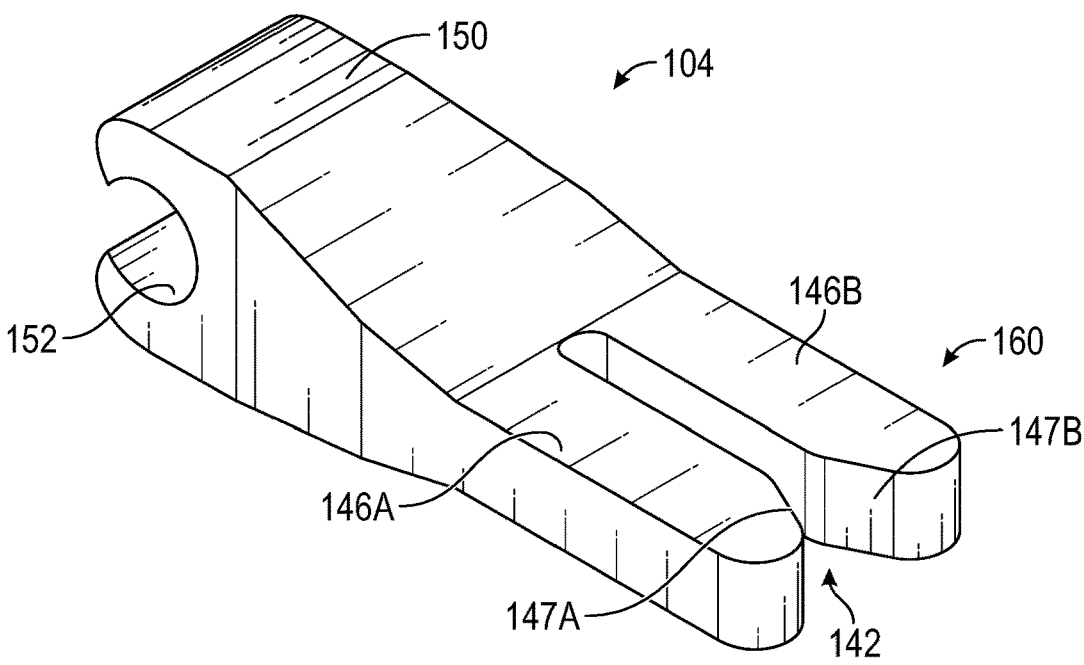
FIG. 4 is a perspective view showing the occluding arm of the catheter stabilizer of FIG. 1.

Referring to FIG. 4, the occluding arm 104 defines a proximal portion 150 and a distal portion 160. The proximal portion 150 of the occluder arm 104 includes a hand 152, which is configured to couple to the engagement rod 130 of the retention body 102, as shown in FIGS. 1 and 2. The hand 152 allows the retention body 102 to be removably coupled to the occluder arm 104 and also allows the occluder arm 104 to be rotated about the axis B (FIG. 1) between the open position (FIG. 1) and the occluding position (FIG. 2). In some embodiments, friction between respective surfaces of the engagement rod 130 of the retention body 102 and the hand 152 of the occluder arm 104 allows the occluder arm 104 to keep a stable position relative to the channel 106. In other embodiments, the occluder arm 104 can snap between the open and occluding position.

The distal portion 160 of the occluding arm 104 defines a free end and includes a receptacle 142 for insertion and occlusion of the catheter 20. As shown, the receptacle 142 has a slotted configuration and defines a first prong 146A and a second prong 146B collectively defining an opening 144 at the distal portion 160 of the occluding arm 104. Each prong 146A and 146B includes a respective tapered shoulder portion 147 defined at the end of each prong 146 to guide the catheter 20 into the receptacle 142. In some embodiments, a width of the receptacle 142 is sufficiently thin to allow the catheter 20 to deform and "pinch" shut when the catheter 20 is fully inserted into the receptacle 142.

Referring to FIGS. 17A-K, 18 and 19, surgical use of the catheter stabilizer 100 is described and illustrated herein. In particular, FIGS. 17A-17K are photographs showing insertion of a ventriculo-atrial shunt during a shunt procedure aided by the catheter stabilizer 100 of FIGS. 1-4. The catheter stabilizer 100 secured a ventricular catheter 20 without assistance from a "second pair of hands" during the shunt procedure while other parts of the shunt procedure were being performed. During the procedure illustrated in FIGS. 17A-17K, a patient (not shown) was positioned in a supine position with a "bump" underneath a right shoulder and a head turned toward the left and their anatomy was registered to an electromagnetic (EM)-based neuronavigation system. It should be noted that the catheter stabilizer 100 allows retraction of cranial tissue and catheter occlusion without interfering with EM neuronavigation such as during use of a metal retractor. The shunt procedure included the following steps: (1) reopening a cranial incision 10 to expose the burr hole 11 drilled into the cranium; (2) placement of the catheter stabilizer 100 into the incision 10 and above the burr hole 11; (3) placement of a transjugular atrial catheter; (4) connection of a ventricular catheter 20 to a valve and the atrial catheter; and (5) removal of the catheter stabilizer 100. As shown in FIGS. 17A and 17B, the catheter stabilizer 100 includes the retention body 102 and the occluder arm 104. In operation, the occluder arm 104 is rotated away from the occluding position to expose the channel 106 (FIG. 17B) and the engagement point 110 for insertion of the cranial securing member 116 into the perforation 113 (FIG. 3) of the engagement point 110. In the embodiment shown, the cranial securing member 116 is a 6 mm self-tapping screw. After additional testing it was found that potential screw compatibility is 6-8 mm but may vary depending on surgeon preference. FIG. 17A also shows a pilot hole 12 drilled in the cranium adjacent to the burr hole 11.

In FIG. 17B, the catheter stabilizer 100 was placed into the incision 10 above the burr hole 11. The incision 10 was held open by a pair of retention members 122 and 124 before the catheter 20 was passed through the channel 106. The cranial securing member 116 is shown being inserted into the pilot hole 12 (visible in FIG. 17A) and the securing member 116 screwed into the pilot hole 12 of the cranium and tightened against the surface 112 of the engagement point 110 in FIG. 17C.

Figure 17D:
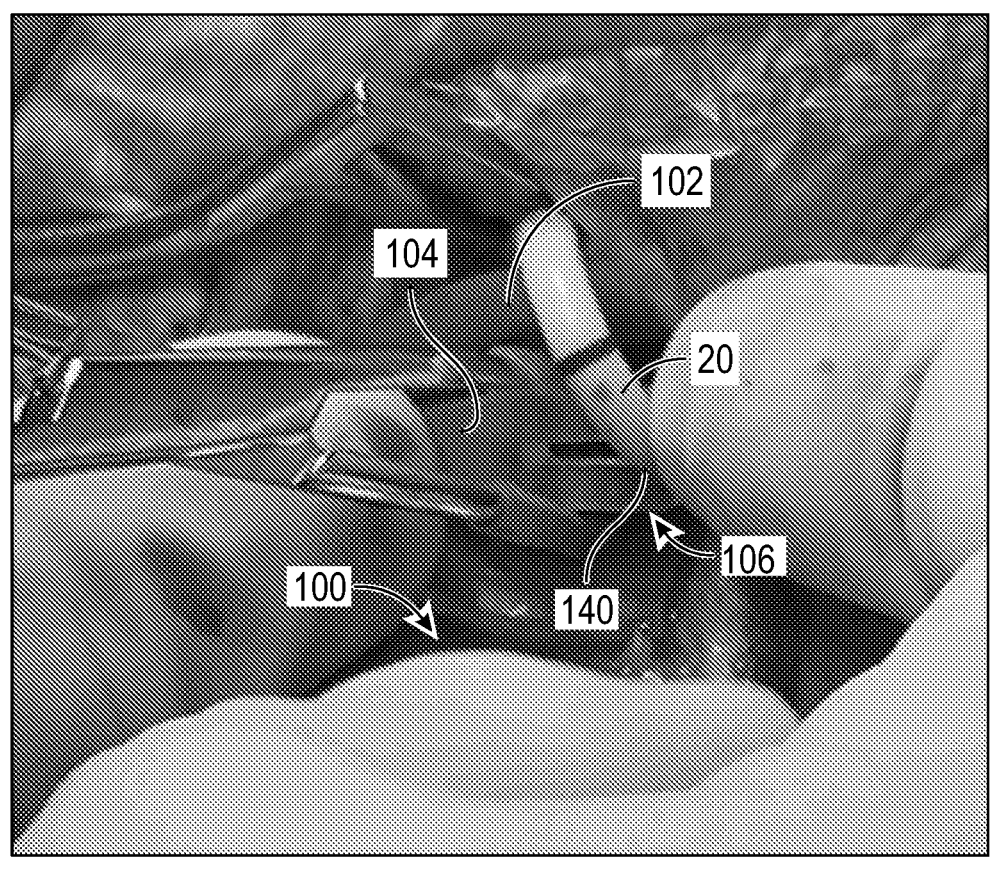
FIG. 17D is a fourth sequential view showing insertion of a ventricular catheter into the occluding arm of the catheter stabilizer of FIG. 1.
Figure 17E:
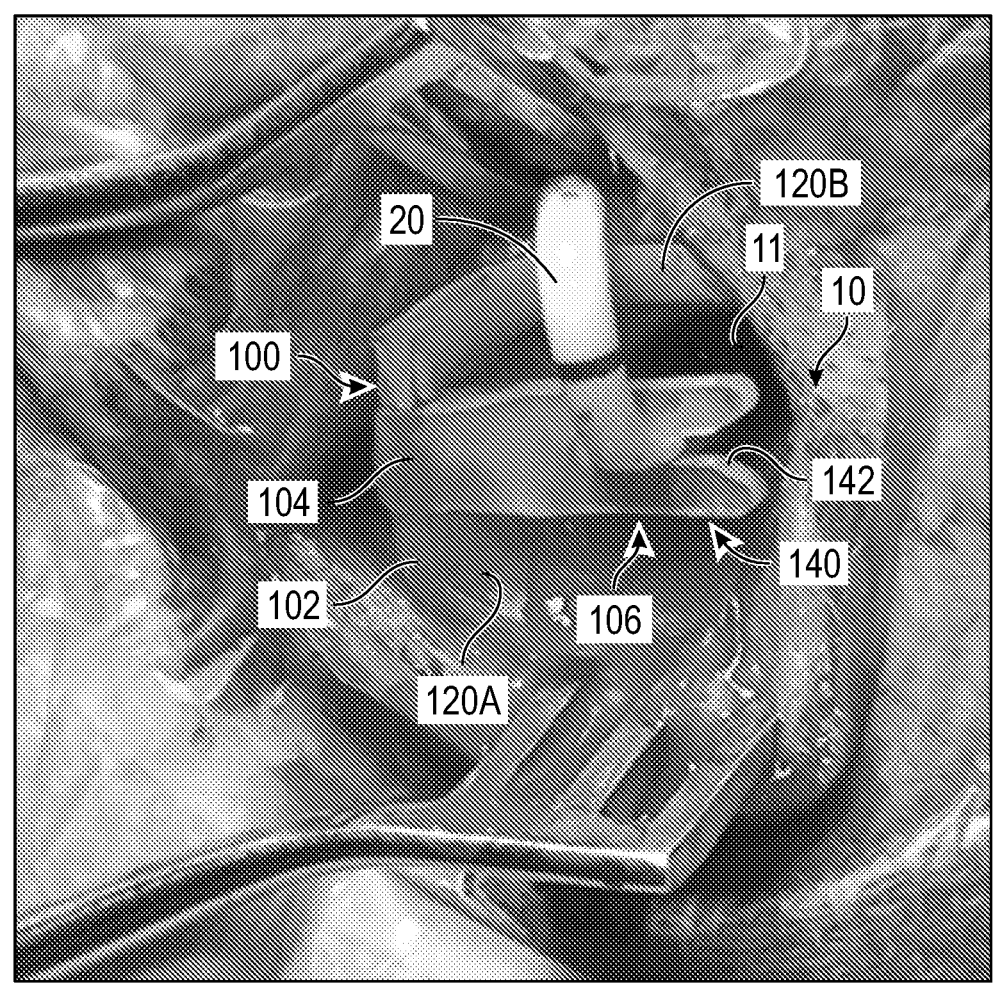
FIG. 17E is a fifth sequential view showing the occluding arm of the catheter stabilizer of FIG. 1 retaining the ventricular catheter within the burr hole.
Figure 17F:
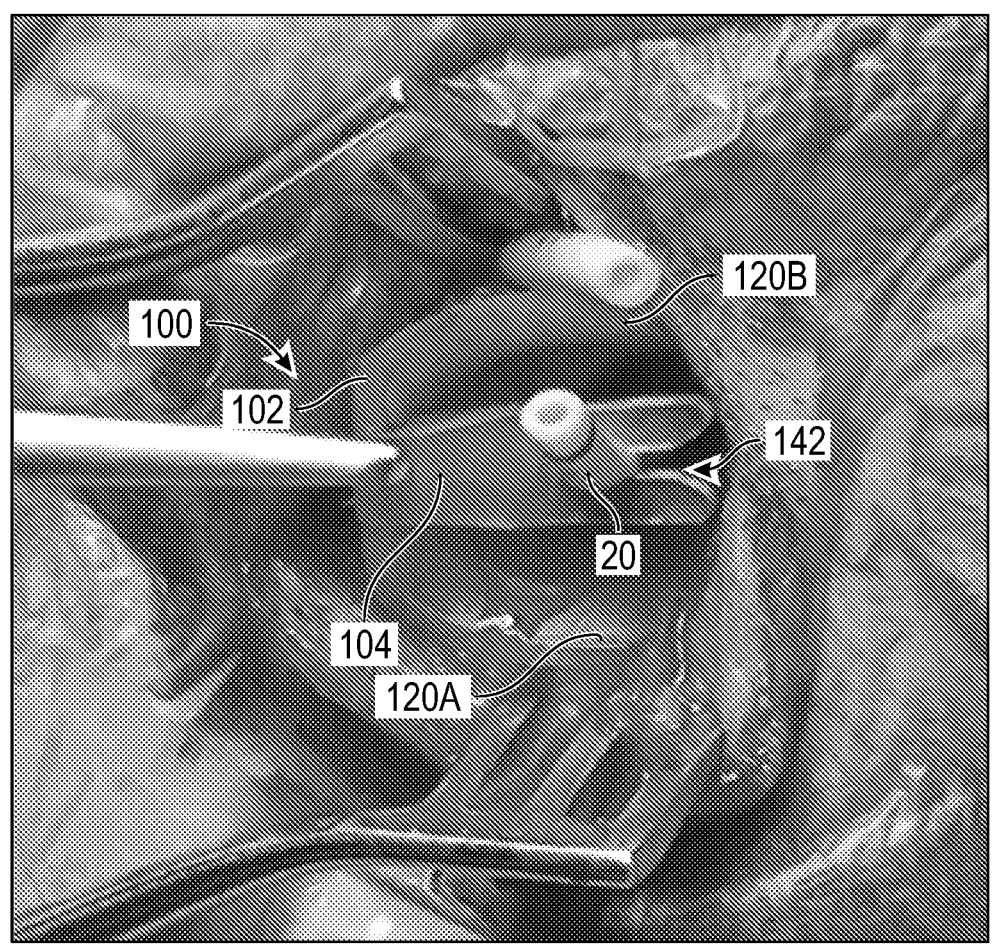
FIG. 17F is a sixth sequential view showing the occluding arm of the catheter stabilizer of FIG. 1 and the ventricular catheter of FIG. 17E having been cut.
Figure 17G:
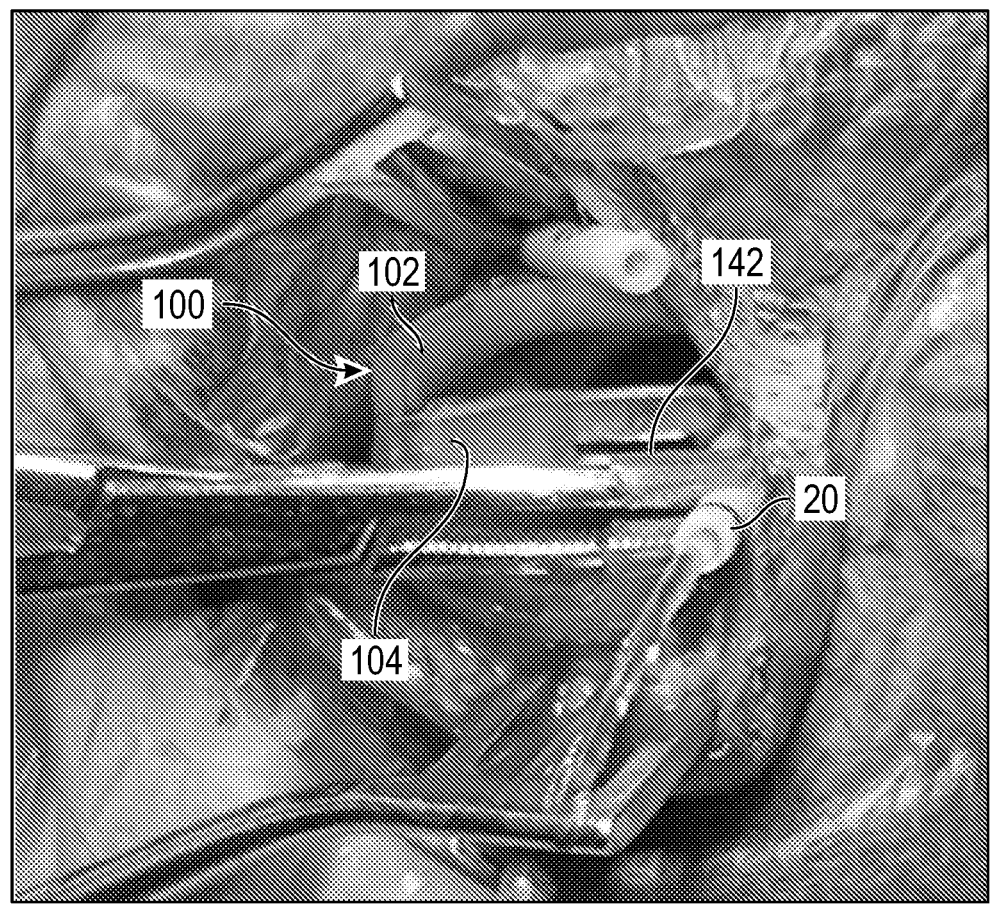
FIG. 17G is a sixth sequential view showing the ventricular catheter of FIG. 17E being removed from the occluding arm of the catheter stabilizer of FIG. 1 to demonstrate an efficacy of the occluding arm, visible by virtue of previously-occluded fluid exiting the catheter.

Referring to FIGS. 17D and 17E, once the catheter stabilizer 100 was secured within the incision 10 and above the burr hole 11, the occluder arm 104 was then rotated about axis B (FIG. 1) to the "occluding" position such that the occluder arm 104 is positioned across the channel 106 and burr hole 11. As shown specifically in FIG. 17D, the catheter 20 was inserted into the distal portion 140 (receptacle 142, visible in FIG. 17E) of the occluder arm 104. In FIG. 17E, the catheter 20 was then captured by the receptacle 142 that communicates with the distal portion 140 of the occluder arm 104. In FIG. 17F, the catheter stabilizer 100 is shown holding the catheter 20 in place within receptacle 142 while the catheter 20 is cut. In FIG. 17G, the catheter 20 is shown moved from the receptacle 142 of the occluder arm 104 with fluid flowing out of the catheter 20 when not occluded by the occluder arm 104, demonstrating the efficacy of the catheter stabilizer 100 when occluding the catheter 20.

Figure 17H:
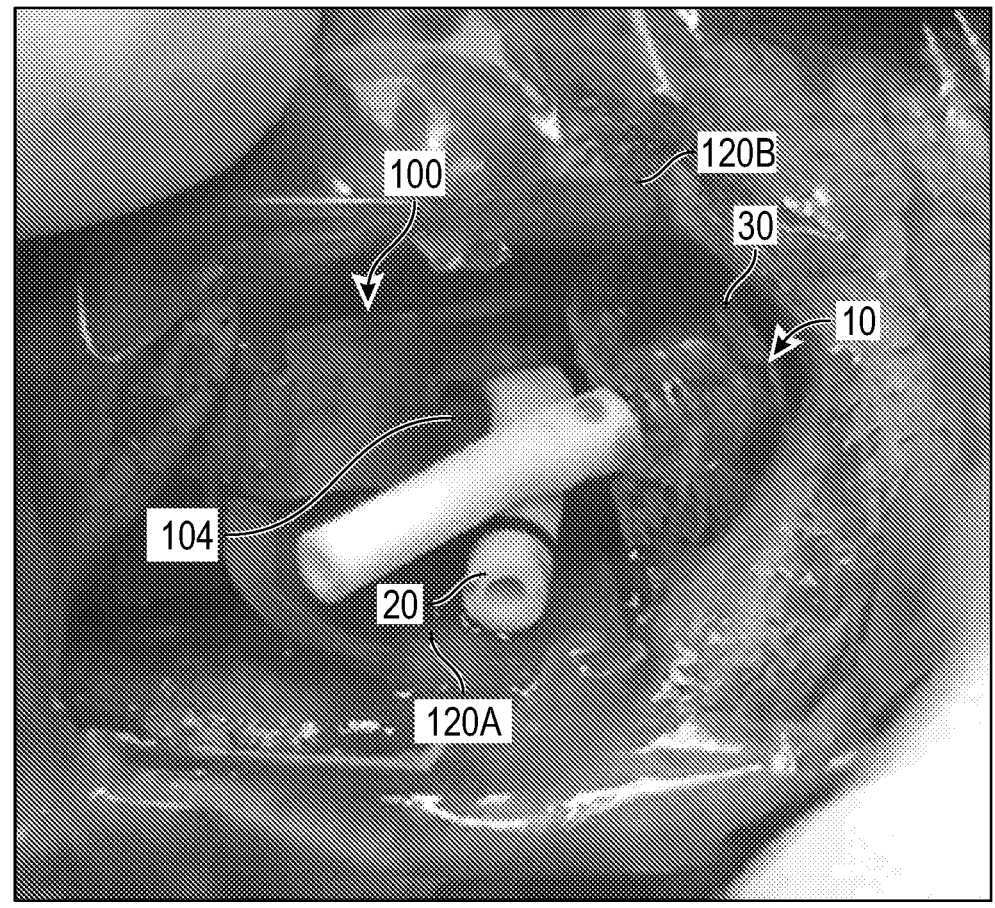
FIG. 17H is a seventh sequential view showing placement of a valve caudal to the catheter while the catheter stabilizer of FIG. 1 holds the catheter in place and retains its position above the burr hole (note that the metal retractor is removed)
Figure 17I:
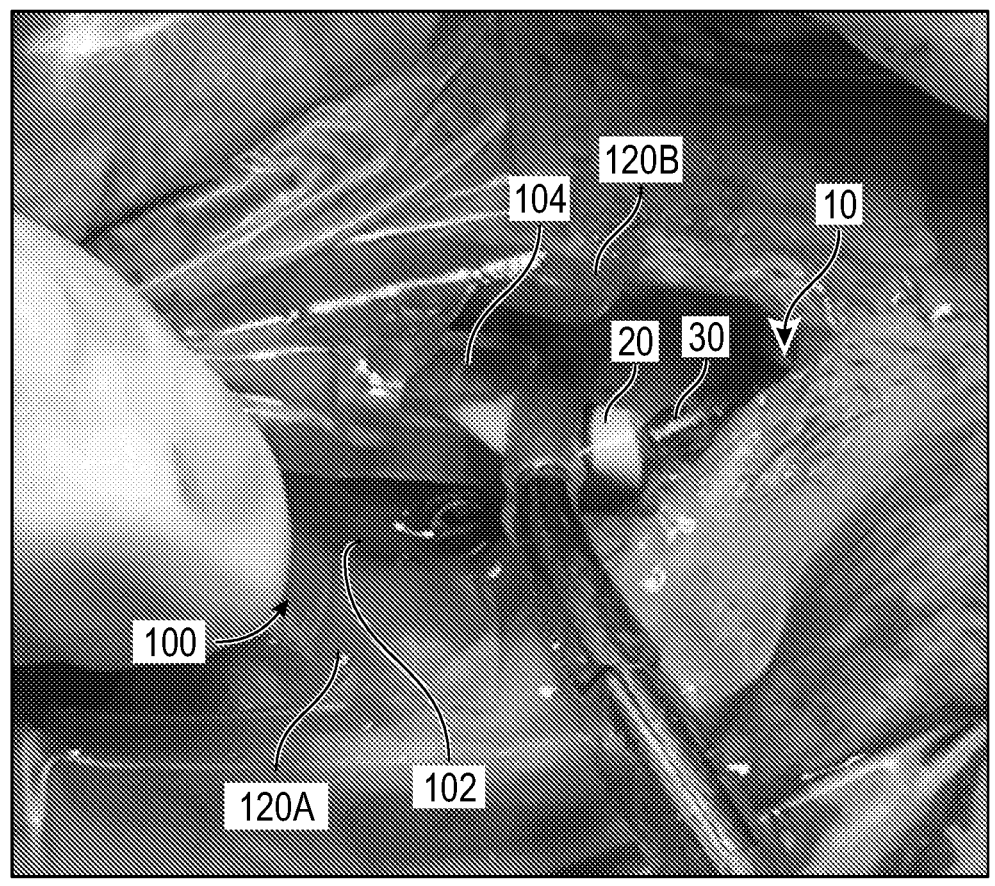
FIG. 17I is an eighth sequential view showing the catheter being engaged with the valve while the catheter stabilizer of FIG. 1 holds the catheter in place and retains its position above the burr hole.
Figure 17J:
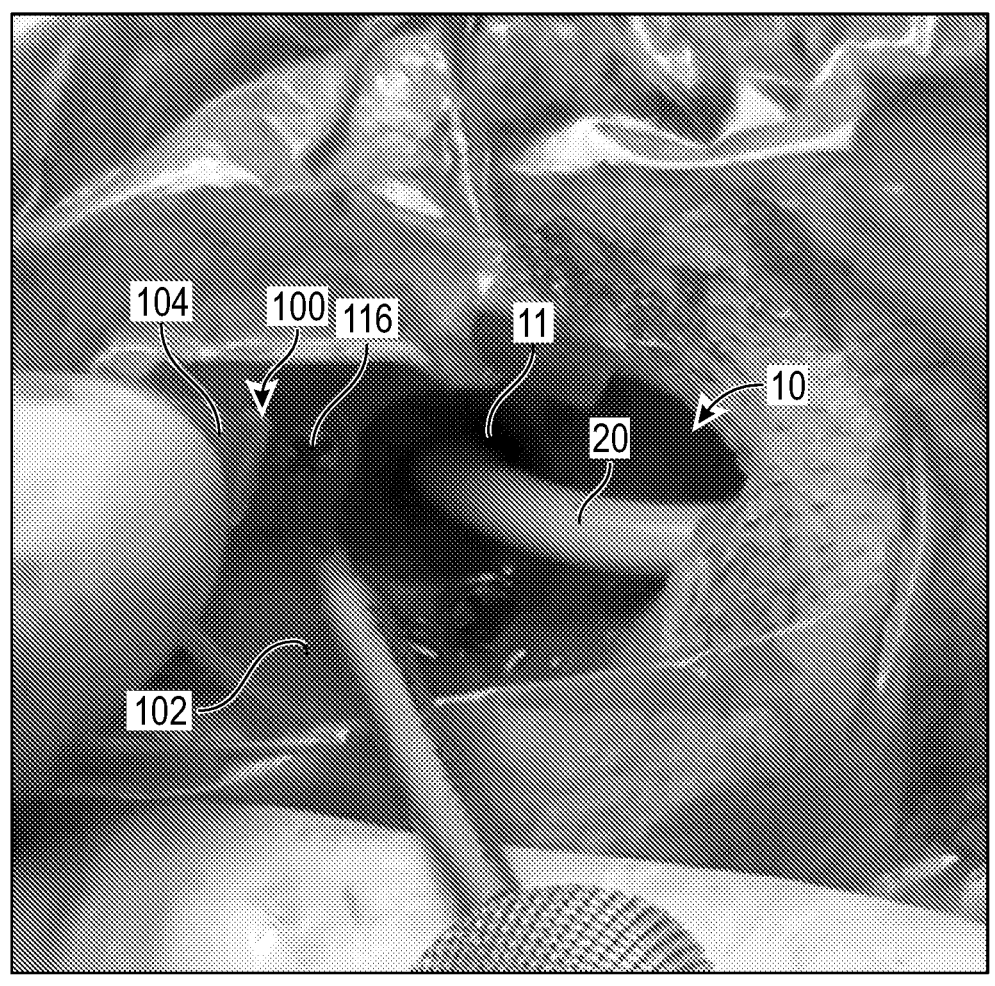
FIG. 17J is a ninth sequential view showing removal of the screw of the catheter stabilizer of FIG. 1.
Figure 17K:
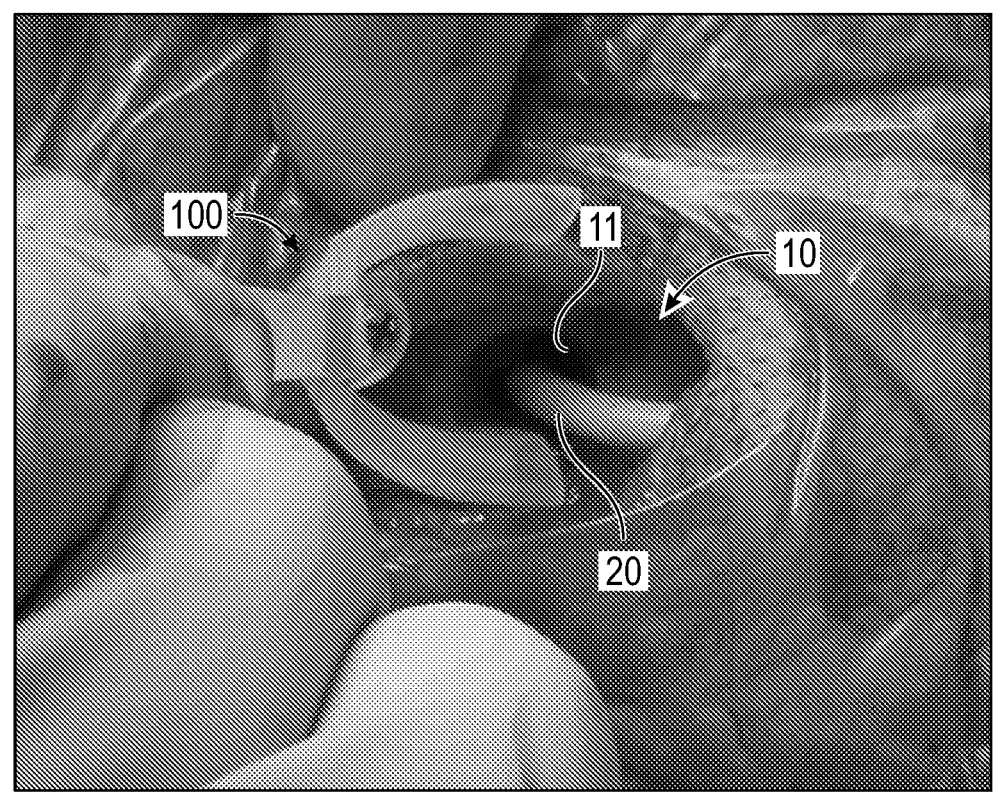
FIG. 17K is a tenth sequential view showing removal of the catheter stabilizer of FIG. 1 from the burr hole.

In FIGS. 17H and 17I, efficacy of the catheter stabilizer 100 when holding the catheter 20 in place during insertion of a valve 30 is demonstrated. During the test, the catheter 20 was held firmly in place and "pinched" shut by the occluder arm 104. The catheter stabilizer 100 remained firmly inside the incision 10 above the burr hole 11 (not visible) during placement of the valve 30 and connection of the valve 30 with the catheter 20. FIGS. 17H and 17I also indicate that the metal retractor was removed during the procedure while the incision 10 remained open and the ventricular catheter 20 remained occluded. The catheter stabilizer 100 does not interfere with the electromagnetic navigation used to identify the trajectory of the ventricular catheter 20. In FIGS. 17J and 17K, to remove the catheter stabilizer 100, the catheter 20 was removed from the receptacle 142 (FIG. 17E) and the occluder arm 104 rotated about the horizontal axis B away from the "occluding" position to expose the securing member 116 of the engagement point 110. In the embodiment shown, the securing member 116 is loosened from the pilot hole 12 and the retention body 102 of the catheter stabilizer 100 is removed from the incision 10.

Figure 8:
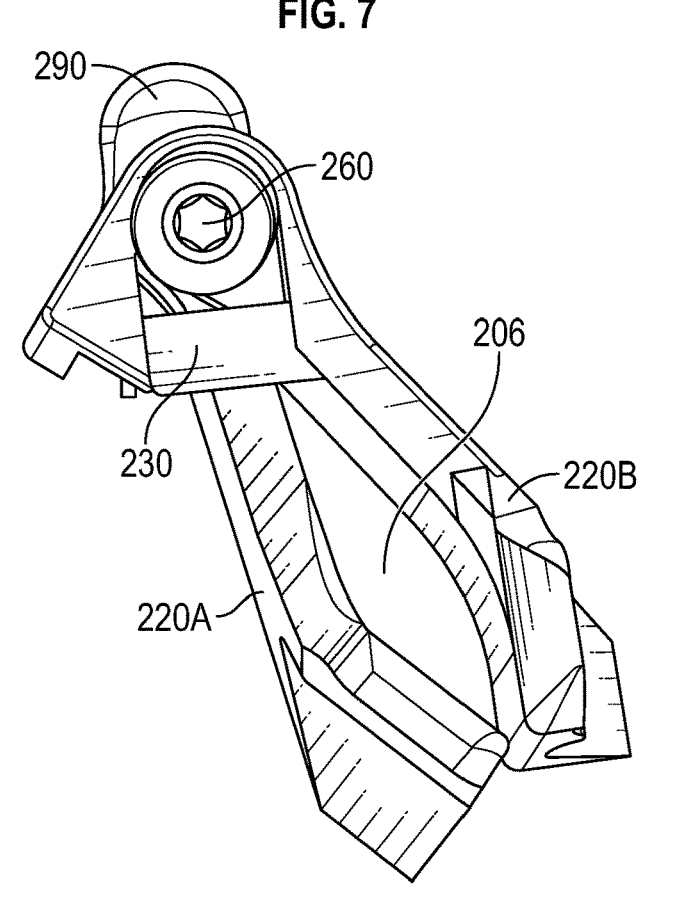
FIG. 8 is a top view showing the catheter stabilizer of FIG. 5 in a "folded" configuration.

Referring to FIGS. 5-8, a second embodiment of a catheter stabilizer 200 is illustrated. Similar to the catheter stabilizer 100 of FIGS. 1-4, the catheter stabilizer 200 includes an occluding arm 204 and a retention body 202 for insertion and engagement within the incision 10 (FIG. 17A) to retain cranial tissue away from the burr hole 11 (FIG. 17A), the retention body 202 including first and second retention members 220A and 220B. As shown, in some embodiments the first and second retention members 220A and 220B are discrete from one another and are pivotably engaged with each other by a pivot element 260. In some embodiments, the first and second retention members 220A and 220B are further associated with one or more tensioning elements 270 to apply force and push apart the first and second retention members 220A and 220B such that cranial tissue is retracted away from the burr hole 11. In some embodiments of the catheter stabilizer 200, the first and second retention members 220A and 220B each include a respective flange 229A and 229B (FIG. 6) to allow a user to grip the retention members 220A and 220B with their fingers during insertion and stabilization of the catheter stabilizer 200 within the incision 10. The flanges 229A and 229B, when "pinched" together by a user, allow the first and second retention members 220A and 220B to be brought together, as shown in FIG. 8. This allows ease of insertion within an incision, with the first and second retention members 220A and 220B being pushed apart again to the position shown in FIGS. 5-7 by tensioning element 270 to retract back cranial tissue. As further shown, retention members 220A and 220B further include respective concave outer surfaces 222A and 222B for engagement with cranial tissue, analogous to concave outer surfaces 122A and 122B of the embodiment of FIG. 1. Similarly, retention members 220A and 220B include respective inner surfaces 224A and 224B that collectively define a channel 206 for passage of a catheter. As shown, the retention body 202 further includes an engagement rod 230 for engagement of the occluding arm 204, and a tail flange 290 (FIG. 7) defined at an apex between the retention members 220A and 220B for additional stabilization of the catheter stabilizer 200 within an incision 10. In some embodiments, tail flange 290 may further include one or more perforations (not shown) for insertion of a securing member such as securing member 116 (FIG. 1) to secure catheter stabilizer 200 to a cranium.

Figure 5:
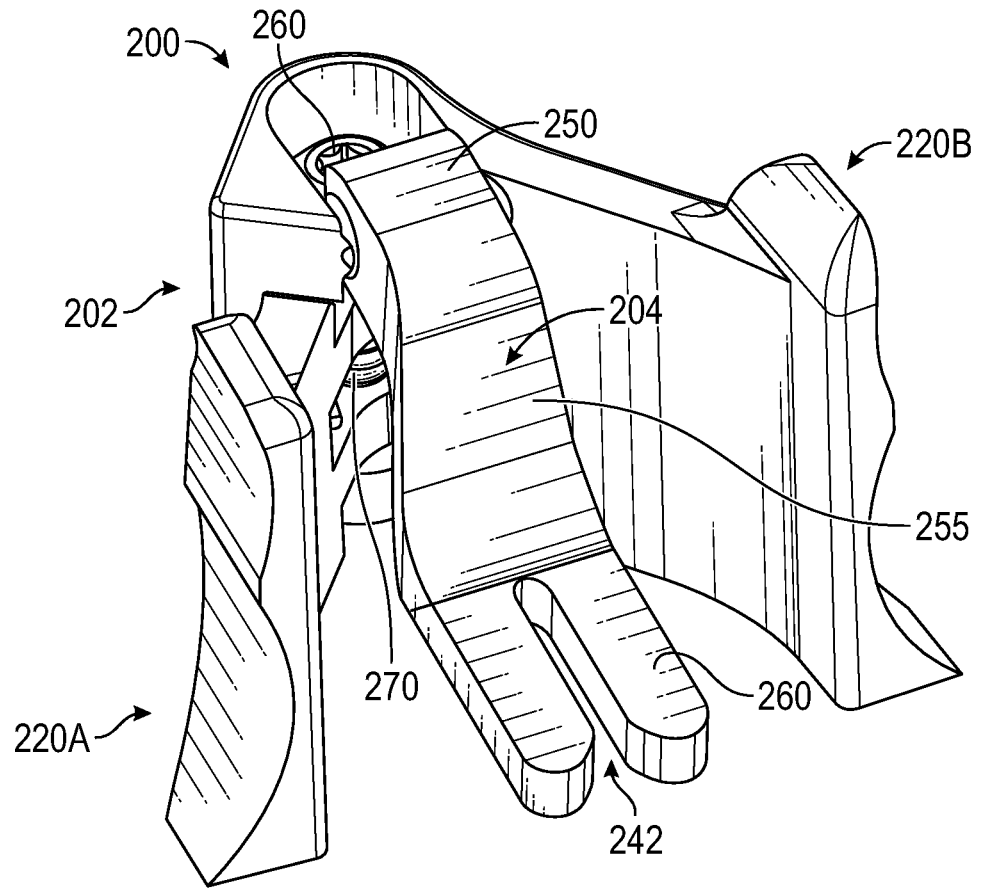
FIG. 5 is a perspective view showing a second embodiment of a catheter stabilizer defining a retention body and an occluding arm.
Figure 6:
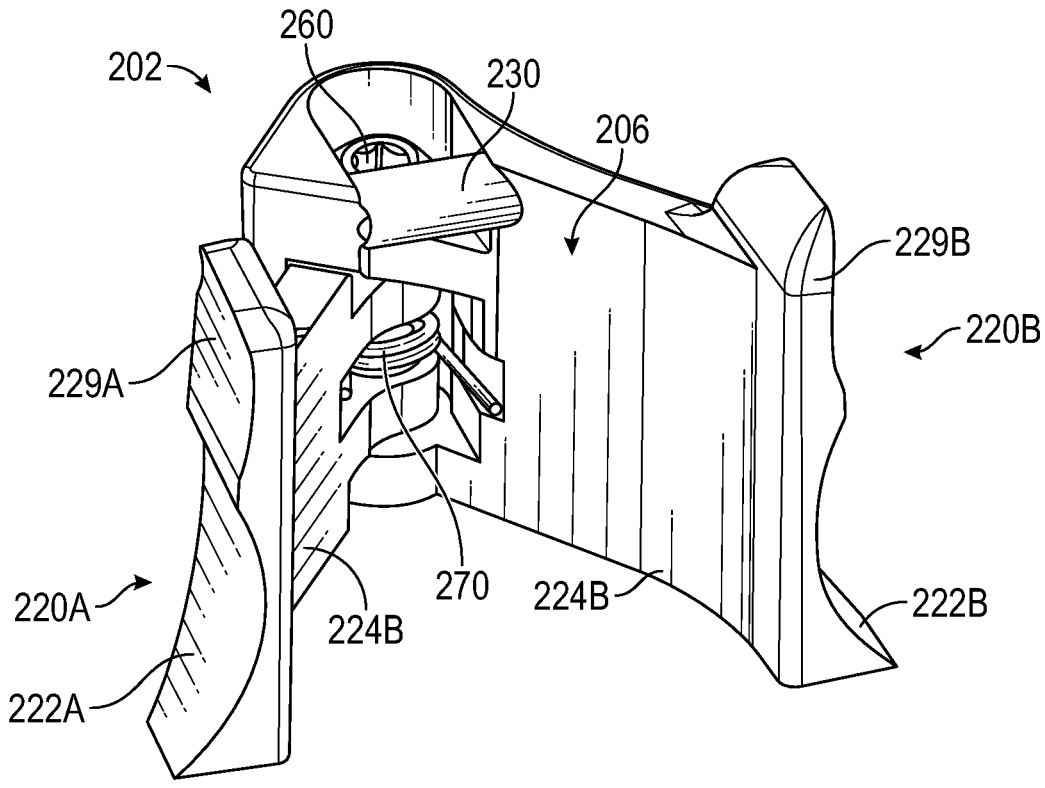
FIG. 6 is a perspective view showing the catheter stabilizer of FIG. 5 with the occluding arm removed.
Figure 7:
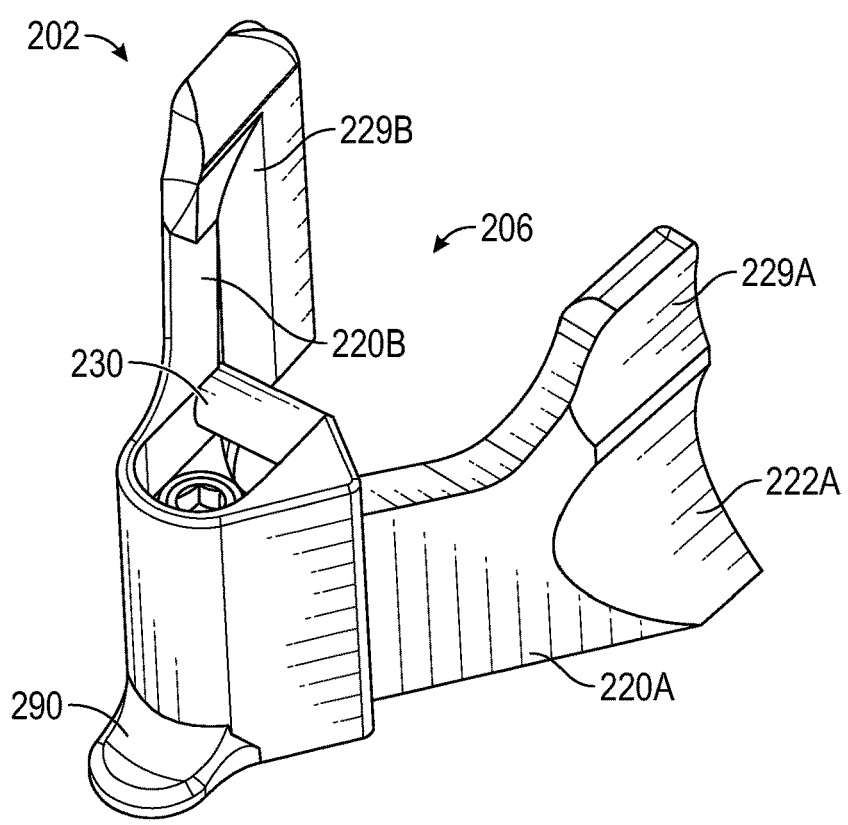
FIG. 7 is a rear perspective view showing the catheter stabilizer of FIG. 5 with the occluding arm removed.

Further, in the embodiment of FIGS. 5-8, the catheter stabilizer 200 includes the occluding arm 204 that is similar in configuration to the occluding arm 104 of the catheter stabilizer 100 of FIGS. 1-4, including a proximal portion 250 and a distal portion 260 defining a free end and a receptacle 242 for insertion of a catheter 20. As shown in FIG. 5, the occluder arm 204 of the catheter stabilizer 200 includes a median portion 255 that defines a "grade" or "z-bend" shape in the occluder arm 204, allowing the occluder arm 204 to "reach" deeper into the channel 206 defined by the catheter stabilizer 200 for receipt of a catheter. It should be noted that in some embodiments, occluder arm 204 including the "z-bend" shaped median portion 255 can be used with the retention bodies 102, 302, 402 and 502 of FIGS. 1-3 and 9-16 to allow for flush contact of the occluder arm 204 with the cranium, improving how the catheter 20 is inserted.

Figure 9:
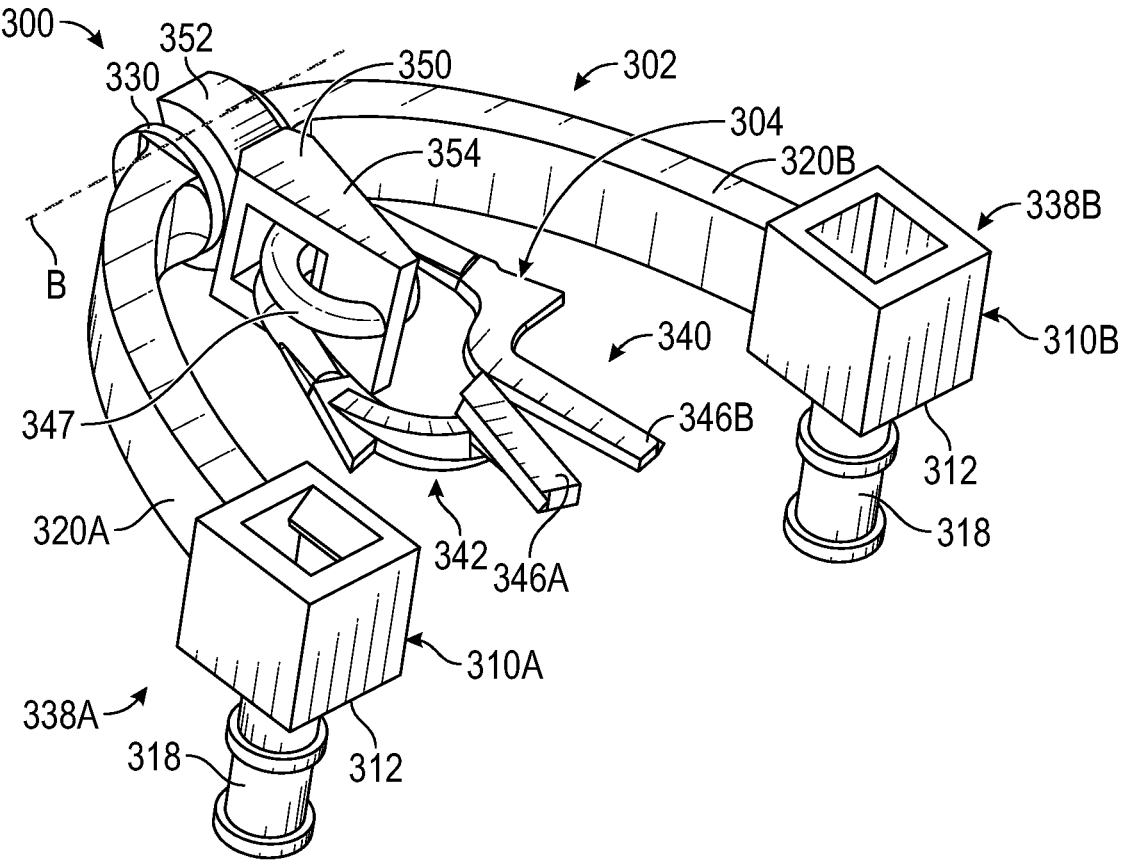
FIG. 9 is a perspective view showing a third embodiment of a catheter stabilizer defining a retention body and an occluding arm.
Figure 10:
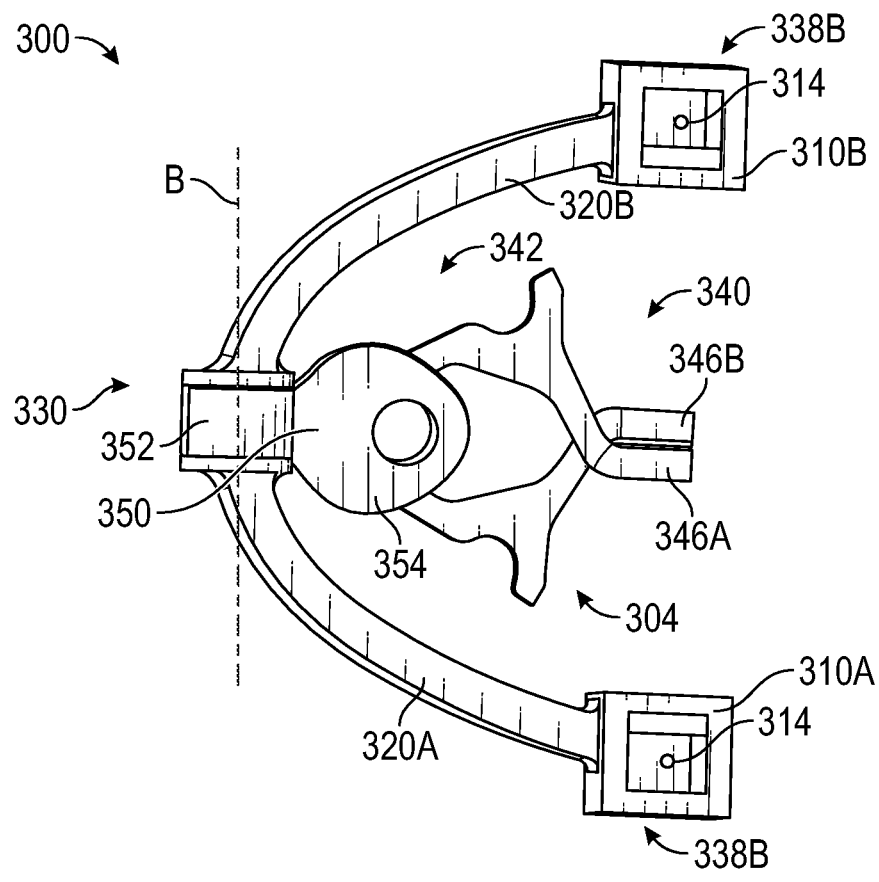
FIG. 10 is a top view showing the catheter stabilizer of FIG. 9.
Figure 11:
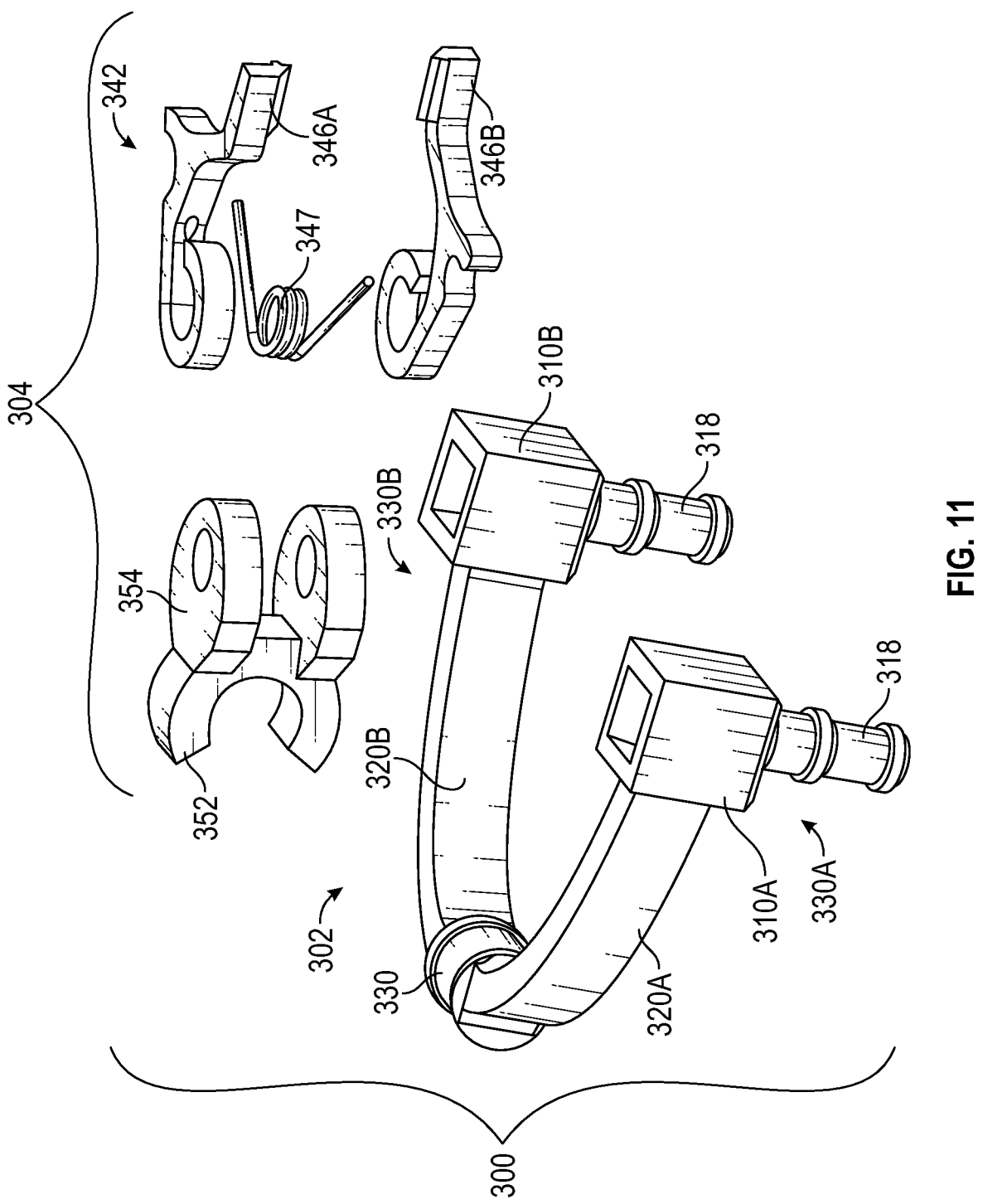
FIG. 11 is an exploded view showing the catheter stabilizer of FIG. 9.

A third embodiment of a catheter stabilizer 300 is shown in FIGS. 9-11. As illustrated, the catheter stabilizer 300 includes a retention body 302 for insertion and engagement within the incision 10 (FIG. 17A) to retain cranial tissue away from the burr hole 11, the retention body 302 including first and second retention members 320A and 320B defining respective distal free ends 338A and 338B. In some embodiments the first and second retention members 320A and 320B integrally form an arc of the retention body 302. As shown, an engagement rod 330 for coupling with an occluder arm 304 is defined at an apex of the arc. Similar to previous embodiments, the occluder arm 304 is operable for rotation about an axis B defined by the engagement rod 330. Referring to FIGS. 9 and 10, the retention body 302 further includes a first engagement point 310A and a second engagement point 310B respectively located at each distal free ends 338A and 338B of each retention member 320A and 320B. The engagement points 310 each include a surface 312 for contacting the cranium with a perforation 314 formed through each surface 312 for insertion of a securing member (not shown) into the cranium to secure the catheter stabilizer 300 to the cranium. In the present embodiment, each engagement point 310 includes an anchor portion 318 for anchoring the retention body 302 into pilot holes (not shown but analogous to pilot hole 12 of FIG. 17A) drilled into the cranium.

As shown in FIGS. 10 and 11, the occluder arm 304 in some embodiments defines a proximal portion 350 and an opposite distal portion 340 defining a free end. The distal portion 340 of the occluder arm 304 includes a receptacle 342 analogous to the respective receptacles 142 and 242 of the catheter stabilizers 100 and 200 and including a first prong 346A and a second prong 346B. In some embodiments, receptacle 342 is a clamp assembly. The first and second prongs 346A and 346B are associated with the proximal portion 350 of the occluder arm 304 by a tensioning element 347 of the receptacle 342 that forces the first and second prongs 346A and 346B to grip and occlude the catheter 20. As shown, the proximal portion 350 includes a hand 352 to couple the occluder arm 304 to the engagement rod 330 of the retention body 302 and a feedthrough portion 354 for receipt of the receptacle 342.

Figures 12, 13:
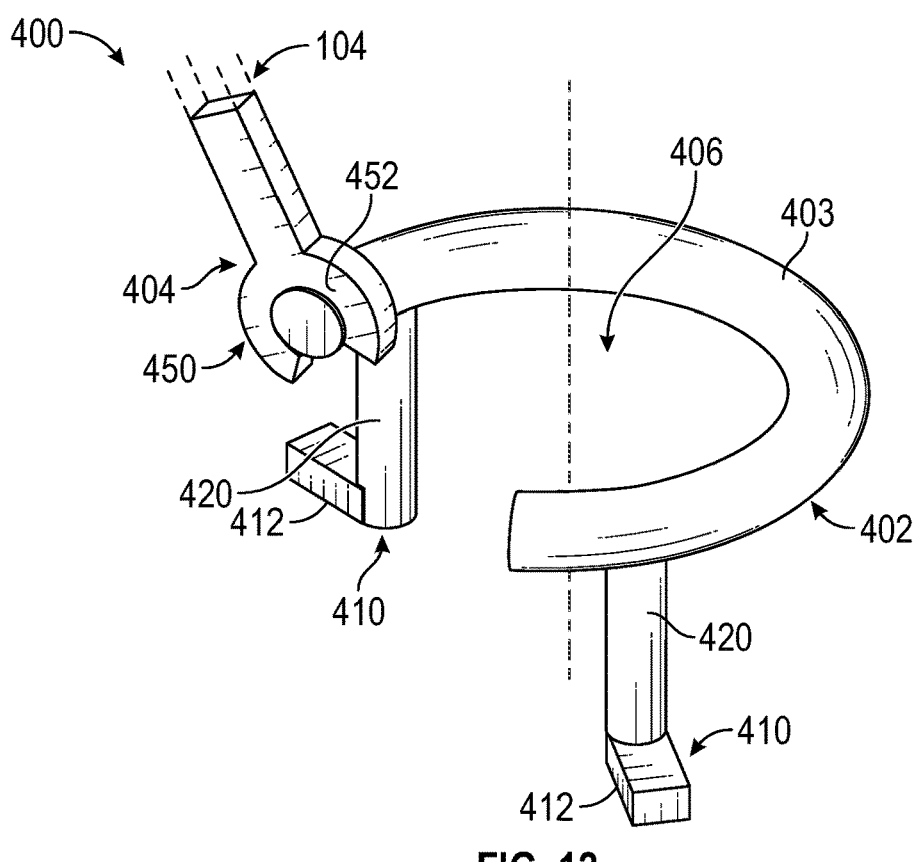
FIG. 12 is a perspective view showing a fourth embodiment of a catheter stabilizer.
FIG. 13 is a perspective view showing the catheter stabilizer of FIG. 12 having a clamping occluding arm.

Referring to FIGS. 12 and 13, a fourth embodiment of a catheter stabilizer 400 is illustrated. As shown, the catheter stabilizer 400 includes a retention body 402 and an occluding arm 404, the retention body 402 forming a channel 406. A distal end (not shown) of occluding arm 404 can be slotted as in the occluding arm of FIG. 4 or can include a clamp assembly as in the occluding arm of FIG. 9. A proximal end 450 can include hand portion 452, similar to embodiments 100, 200 and 300 of FIGS. 4, 5, and 9. In the present embodiment, an engagement rod 403 forms the majority of the retention body 402 such that various embodiments of the occluding arm 404 can be placed anywhere on the engagement rod 403. In some embodiments, more than one occluding arm 404 can be coupled to the engagement rod 403 in order to stabilize and occlude more than one catheter 20. In other embodiments, the occluding arm 404 can resemble a "scissor" configuration, as shown in FIG. 13. The retention body 402 of the catheter stabilizer 400 can include a plurality of retention members 420 to retract cranial tissue which, in the embodiment shown, can align with an axis defined by the channel 406 and the burr hole 11. In some embodiments, any number of retention members 420 can be included. In the embodiments of FIGS. 12-13, the retention members 420 are each associated with a respective engagement point 430 defining a surface 412 and a perforation (not shown) for engagement with a securing member (not shown).

Figure 14:
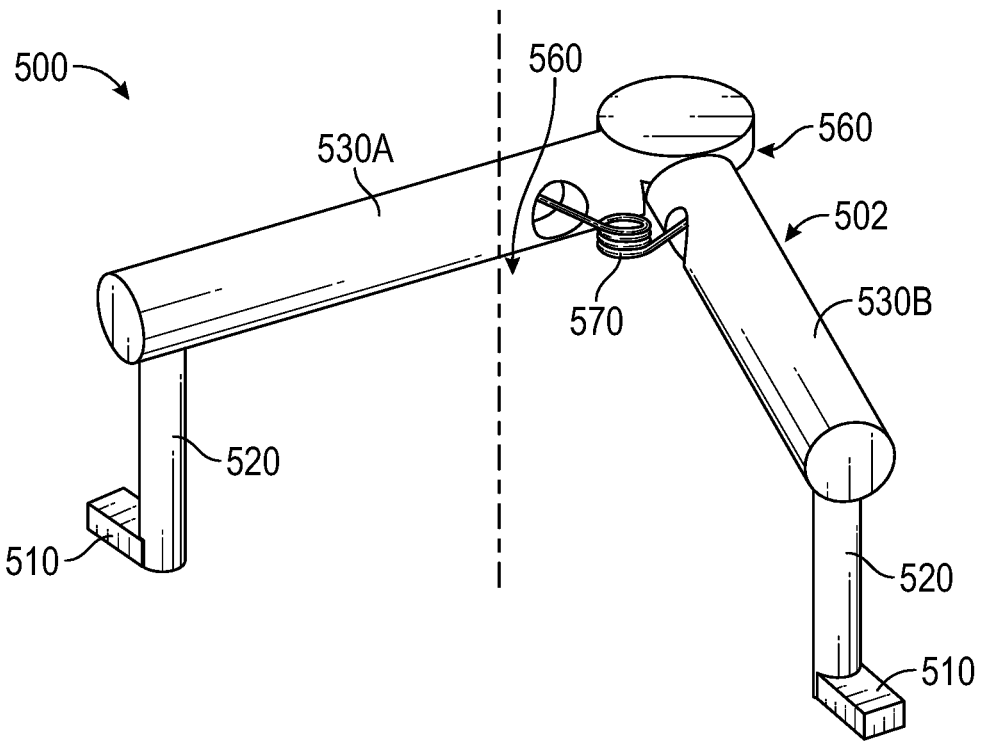
FIG. 14 is a perspective view showing a fifth embodiment of a catheter stabilizer.
Figure 15:
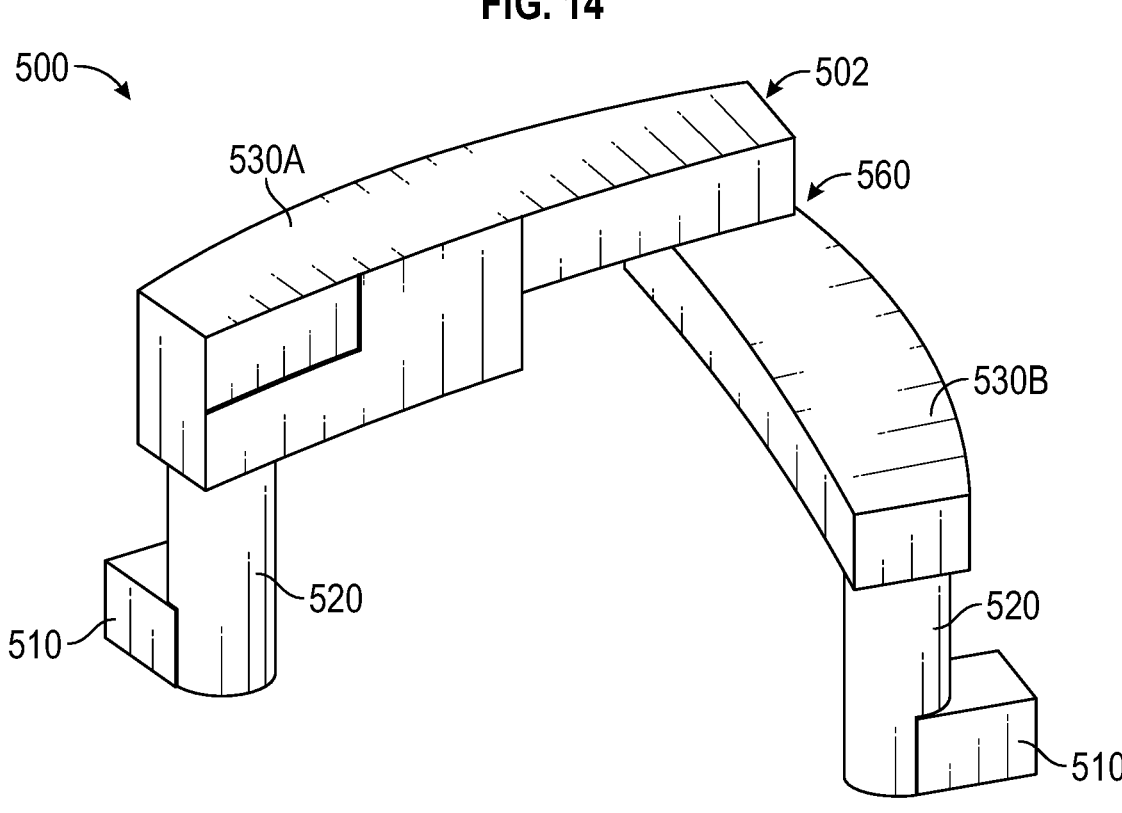
FIG. 15 is a front perspective view showing a sixth embodiment of a catheter stabilizer.
Figure 16:
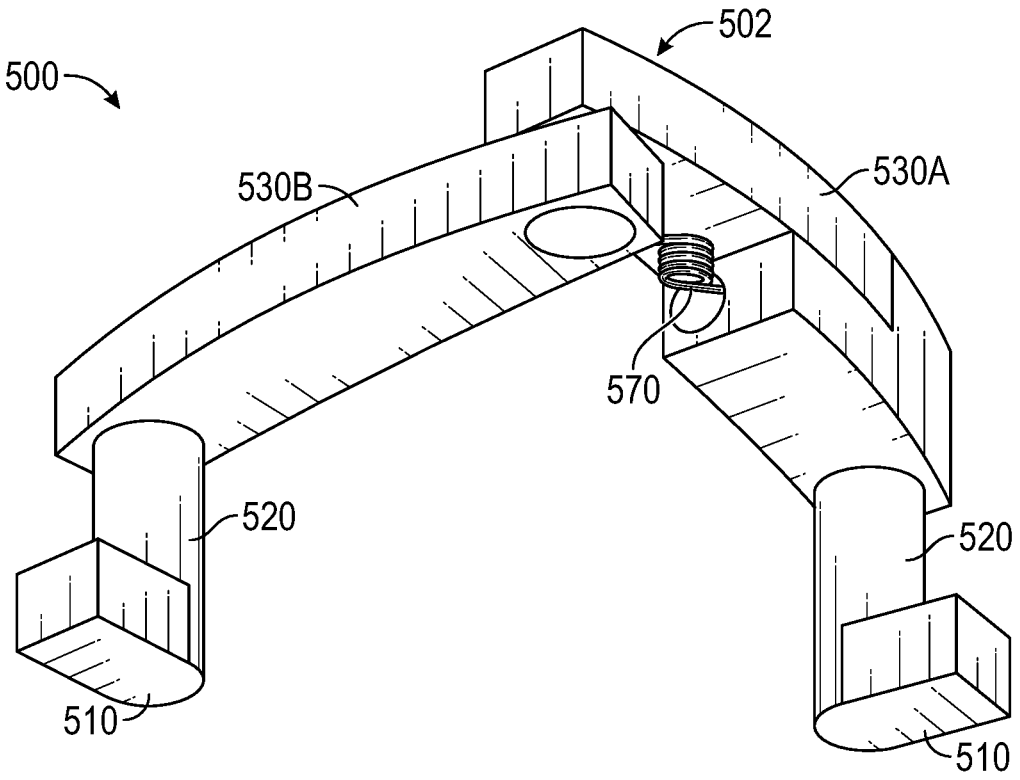
FIG. 16 is a rear perspective view showing the catheter stabilizer of FIG. 15.

Referring to FIGS. 14-16, a fifth embodiment of a catheter stabilizer 500. As shown, the catheter stabilizer 500 includes a retention body 502, which in some embodiments, may define a joint or pivot element 560 linking a first engagement rod 530A and a second engagement rod 530B with each engagement rod 530 being configured to receive an occluding arm (not shown). Suitable occluding arms for use with retention body 502 can include occluding arms 104 (FIG. 4), occluding arms 204 (FIG. 5) and 304 of FIG. 9. In operation, the engagement rods 530A and 530B are tensioned away from each other by tensioning element 570 to retract back cranial tissue. Similarly to the previous embodiment, the retention body 502 of the catheter stabilizer 500 can include a plurality of retention members 520 to retract cranial tissue which, in the present embodiment, can align with an axis defined by a channel 506 and the burr hole 11. In some embodiments, any number of retention members 520 can be included. The retention members 520 are each associated with an engagement point 510 defining a surface 612 and a perforation (not shown) for engagement with a securing member (not shown). Referring to FIGS. 15-16, in some embodiments the engagement rods 530A and 530B can be "wide" enough to both engage an appropriate occluding arm and retract back cranial tissue.

Referring to FIGS. 18 and 19, a method 700 for insertion of a catheter stabilizer 100 within an incision 10 is illustrated. For ease of review, components of the catheter stabilizer 100 are described with respect to embodiment 100 shown in FIGS. 1-4; however, various other embodiments are contemplated herein for use with methods 700 and 750, as discussed above. Photographic images of each step in the method 700 are shown in FIGS. 17A-17E. At block 701 (FIG. 17A), one or more securing members 116 are inserted into the catheter stabilizer 100. At block 702 (FIG. 17B), the catheter stabilizer 100 is positioned over a burr hole including a catheter and cranial tissue is retracted away from the burr hole by retention members 120A and 120B of catheter stabilizer 100. At block 703 (FIG. 17C), the catheter stabilizer 100 is secured to a cranium by the one or more securing members 116. At block 704 (FIG. 17D), the occluding arm 104 of the catheter stabilizer 100 is lowered into an "occlusion" position (shown in FIG. 2) above the burr hole and the channel defined by retention members 120A and 120B. At block 705 (FIG. 17E), the catheter is inserted into the occluding arm 104 and "pinched" shut by the occluding arm 104.

A method 750 for subsequent removal of the catheter stabilizer 100 is shown in FIG. 19. Photographic images illustrating each step in the method 750 are shown in FIGS. 17G, 17J and 17K. At block 706 (FIG. 17G), the catheter 20 is removed from the occluding arm 104. At block 707 (FIG. 17J), the occluding arm 104 is raised away from the "occlusion" position above the burr hole to expose the channel 106. At block 708 (FIG. 17J), the one or more securing members 116 are removed or loosened within their pilot holes. At block 709 (FIG. 17K), the catheter stabilizer 100 is then carefully removed from the incision 10.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A catheter stabilizer apparatus, the catheter stabilizer apparatus including;

a retention body including:

one or more retention members in association with the retention body; and a channel collectively defined by the one or more retention members, wherein the channel defines a vertical axis A; and an occluding arm defining a proximal portion and a distal portion, the proximal portion of the occluding arm being pivotably engaged with the retention body such that the occluding arm is operable for being lowered across the channel to an occluding position, and the distal portion of the occluding arm defining a receptacle, wherein the retention body further comprises a tensioning element configured for applying tension to the one or more retention members such that the one or more retention members are pushed apart.

2. The catheter stabilizer apparatus of claim 1, wherein the receptacle defines a slotted configuration, wherein the receptacle is configured to receive a catheter such that fluid flow from the catheter is prevented.

3. The catheter stabilizer apparatus of claim 1, wherein the proximal portion of the occluding arm is pivotably engaged with the retention body such that the occluding arm is rotated about horizontal axis B between a peripheral position and the occluding position.

4. The catheter stabilizer apparatus of claim 3, wherein the occluding arm is positioned over the channel perpendicular to the horizontal axis B when the occluding arm is in the occluding position.

5. The catheter stabilizer apparatus of claim 1, wherein each retention member of the one or more retention members defines a concave outer surface.

6. The catheter stabilizer apparatus of claim 5, wherein each of the one or more retention members defines a flange portion located above the concave outer surface.

7. The catheter stabilizer apparatus of claim 1, wherein each retention member of the one or more retention members defines an inner surface, wherein the arrangement of the inner surfaces of each retention member of the one or more retention members collectively defines the channel.

8. The catheter stabilizer apparatus of claim 1, wherein the retention body includes an engagement rod and wherein the engagement rod defines a horizontal axis B.

9. The catheter stabilizer apparatus of claim 8, wherein the engagement rod is located at a junction between each of the one or more retention members.

10. The catheter stabilizer apparatus of claim 8, wherein the occluding arm is removably coupled to the engagement rod.

11. The catheter stabilizer apparatus of claim 1, wherein the proximal portion of the occluding arm defines a hand, wherein the hand is configured to be removably coupled to the retention body.

12. The catheter stabilizer apparatus of claim 1, wherein the retention body includes at least one engagement point for insertion of a securing member.

13. The catheter stabilizer apparatus of claim 12, wherein the at least one engagement point includes a perforation defined through a surface, wherein the perforation is configured to receive the securing member.

14. The catheter stabilizer apparatus of claim 1, wherein the occluding arm includes a medial portion such that the distal portion of the occluding arm is located within the channel.

15. The catheter stabilizer apparatus of claim 1, wherein the occluding arm and the retention body are comprised of a non-ferromagnetic material.

* * * * *